July 7, 1964 J. M. GARABEDIAN Plant Pat. 2,419
NECTARINE TREE
Filed July 5, 1963
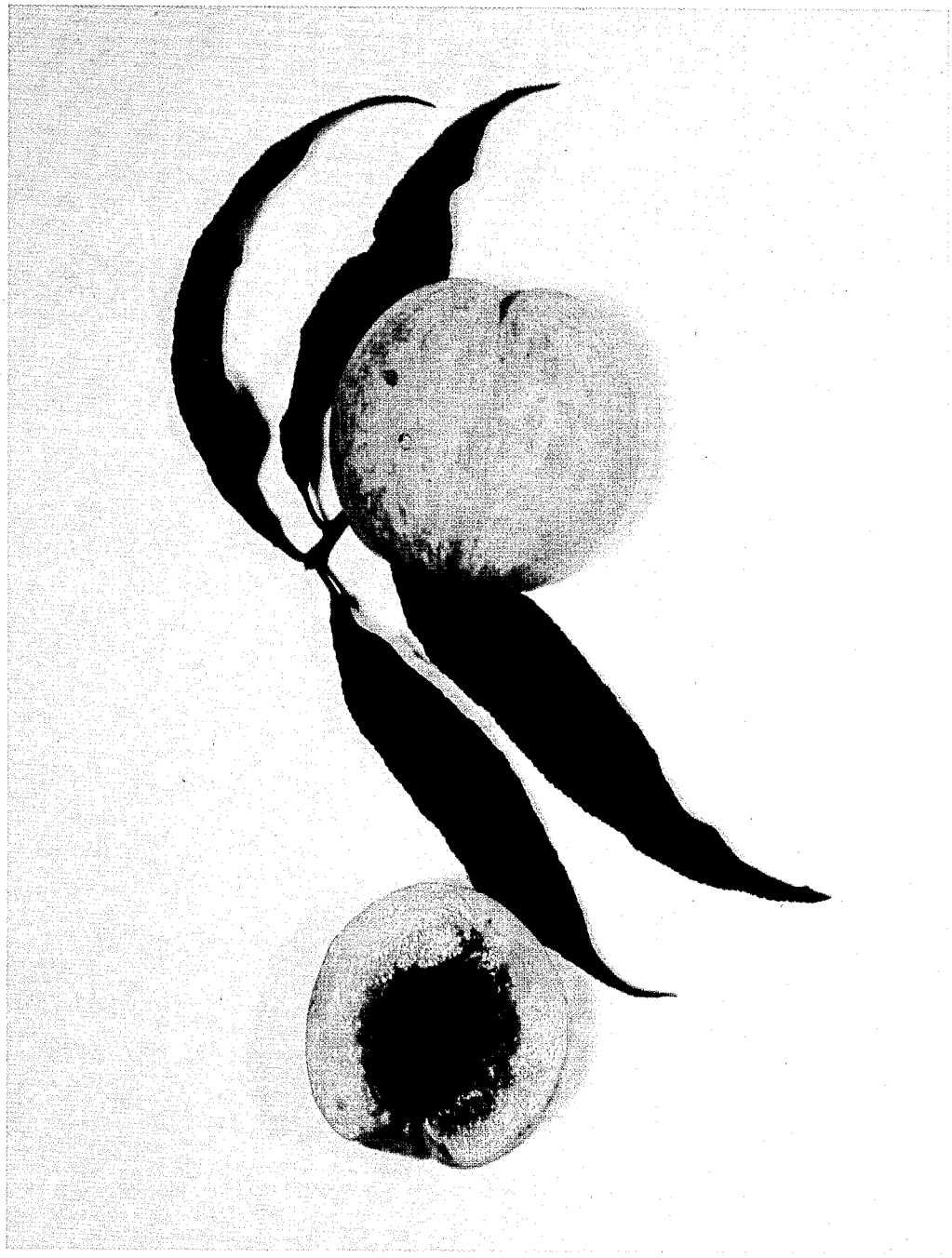
INVENTOR
John M. Garabedian
Webster & Webster
ATTYS.

United States Patent Office

Plant Pat. 2,419
Patented July 7, 1964

2,419
NECTARINE TREE

John M. Garabedian, Fresno, Calif., assignor to Peach & Willow Farms, Fresno, Calif., a corporation of California Filed July 5, 1963, Ser. No. 293,218
1 Claim. (Cl. Plt.—41)

This invention relates to a new and distinct variety of nectarine tree which is a regular and productive bearer of late ripening, large, uniform, globose, clingstone fruit; such fruit being characterized by yellow flesh having red near the stone, and by yellow skin overspread to a large extent with red which is streaked and mottled.

In comparison with the Gold King nectarine (United States Plant Patent No. 1,424), which it most nearly resembles, the fruit of the present variety is further characterized by a deeper ventral suture toward the apex, and by a later ripening period such that the harvest is approximately four weeks after said Gold King nectarine.

The herein claimed variety of nectarine tree was originated by me, under conditions of careful and continuing observation, in an experimental nursery at a ranch located near Fresno, county of Fresno, California; the original tree being one of a number of seedlings grown from a group of seeds of unknown parentage.

When such seedlings reached maturity, and the novel and distinctive characteristics of the one which is the present variety were recognized by me, I selected it for reproduction in view of its apparent commercial potential.

Thereafter, asexual reproduction of the variety was accomplished, under my control and direction, by budding on mature trees in an experimental orchard on the ranch located as aforesaid; such reproductions, in maturity, having run true to the original tree in all respects.

The drawing comprises an illustration, by photographic reproduction in color, of one fruit in elevation with leaves, and a half of another fruit cut to show the flesh and with the stone remaining in place.

Referring now more specifically to the pomological details of this new and distinct variety of nectarine tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Spreading.
- *Form.*—Vase shaped.
- *Hardiness.*—Hardy.
- *Production.*—Very productive.
- *Bearing.*—Regular bearer.

Trunk:
- *Form.*—Medium.
- *Texture.*—Medium.

Branches:
- *Form.*—Medium.
- *Texture.*—Medium.
- *Color.*—Brown.
- *Lenticels.*—Medium number.

Leaves:
- *Size.*—Medium. Average length—6½". Average width—1½".
- *Form.*—Acuminate; acutely pointed.
- *Thickness.*—Medium.
- *Color.*—Top side—medium green (23–L–11). Under side—light green (21–K–6).
- *Texture.*—Smooth.
- *Margin.*—Crenate.
- *Petiole.*—Medium length.
- *Glands.*—Average number—four. Medium size; reniform; positioned on blade and petiole.
- *Stipules.*—Wanting.

Flower Buds:
- *Hardiness.*—Hardy.
- *Size.*—Large.
- *Length.*—Medium.

Flowers:
- *Blooming period.*—March 5th to March 10th. Medium as compared with other varieties.
- *Size.*—Large.
- *Color.*—Pink.

Fruit:
- *Maturity when described.*—Eating ripe.
- *Date of first picking.*—September 20th.
- *Date of last picking.*—October 5th.
- *Size.*—Uniform; large. Average diameter axially—3¼". Average transversely in suture plane—3⅜".
- *Form.*—Uniform; globose; slightly compressed on ventral side toward apex.
- *Suture.*—Distinct. Shallow, becoming deeper toward apex. Extends from base to slightly beyond apex.
- *Ventral surface.*—Compressed slightly toward apex. Lips—equal.
- *Cavity.*—Rounded. Elongated slightly in suture plane with suture showing on one side. Average depth—½". Average breadth—⅝".
- *Base.*—Rounded.
- *Apex.*—Short; slightly depressed.

Skin:
- *Thickness.*—Medium.
- *Texture.*—Medium.
- *Tenacity.*—Tenacious to flesh.
- *Tendency to crack.*—Slight, at suture toward apex.
- *Down.*—Wanting.
- *Color.*—Yellow (9–L–5) overspread to a large extent with red (3–K–10) shading to (5–L–6) which is streaked and mottled.

Flesh:
- *Color.*—Yellow (9–L–2) with red (4–K–6 to 6–K–6) adjacent the stone.
- *Amygdalin.*—Moderate.
- *Texture.*—Firm.
- *Fibers.*—Few; tender.
- *Ripens.*—Evenly.
- *Flavor.*—Slightly acid.
- *Aroma.*—Distinct.
- *Eating quality.*—Good.

Stone:
- *Type.*—Clingstone; adheres to flesh over entire surface.
- *Size.*—Medium. Average length—1¾". Average breadth—1¼". Average thickness—⅞".
- *Form.*—Ovoid.
- *Hilum.*—Oblong.
- *Apex.*—Acute.
- *Sides.*—Equal.
- *Surface.*—Irregularly furrowed near base; ridged from base to above center.
- *Ridges.*—Rounded; continuous.
- *Pits.*—Elongated.
- *Ventral edge.*—Thin.
- *Dorsal edge.*—Full.
- *Color.*—Brown (14–B–11).
- *Tendency to split.*—Slight.

Use: Market.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

The following is claimed:

A new and distinct variety of nectarine tree, substantially as illustrated and described, characterized by regular and productive bearing of large, uniform, globose, clingstone fruit having yellow flesh with red adjacent the stone, and yellow skin largely overspread with red which is streaked and mottled; and further characterized, in comparison to the Gold King nectarine, by fruit having a deeper ventral suture toward the apex, and by a harvest period about four weeks later.

No references cited.